(12) United States Patent
Joseph et al.

(10) Patent No.: US 8,465,977 B2
(45) Date of Patent: Jun. 18, 2013

(54) METHOD AND APPARATUS FOR LIGHTED TEST STRIP

(75) Inventors: Abner David Joseph, Carmel, IN (US); Brian A. Heald, Fortville, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 975 days.

(21) Appl. No.: 12/177,328

(22) Filed: Jul. 22, 2008

(65) Prior Publication Data

US 2010/0021342 A1    Jan. 28, 2010

(51) Int. Cl.
*G01N 33/49* (2006.01)

(52) U.S. Cl.
USPC ........... 436/63; 436/69; 436/95; 436/164; 422/404; 422/410; 422/82.05

(58) Field of Classification Search
USPC ............... 422/404, 410, 82.05; 436/63, 69, 436/95, 164
See application file for complete search history.

(56) References Cited

U.S. PATENT DOCUMENTS

| | | |
|---|---|---|
| 4,432,366 A | 2/1984 | Margules |
| 5,228,972 A | 7/1993 | Osaka et al. |
| 5,304,468 A | 4/1994 | Phillips et al. |
| 5,320,732 A | 6/1994 | Nankai et al. |
| 5,395,504 A | 3/1995 | Saurer et al. |
| 5,407,554 A | 4/1995 | Saurer |
| 5,547,702 A | 8/1996 | Gleisner |
| 5,563,042 A | 10/1996 | Phillips et al. |
| 5,651,869 A | 7/1997 | Yoshioka et al. |
| 5,686,829 A | 11/1997 | Girault |
| 5,997,817 A | 12/1999 | Crismore et al. |
| 6,201,607 B1 | 3/2001 | Roth et al. |
| 6,514,460 B1 | 2/2003 | Fendrock |
| 6,830,551 B1 * | 12/2004 | Uchigaki et al. ............ 600/584 |
| 6,847,451 B2 | 1/2005 | Pugh |

(Continued)

FOREIGN PATENT DOCUMENTS

| | | |
|---|---|---|
| EP | 0 407 800 A2 | 1/1991 |
| EP | 1 199 978 B1 | 5/2002 |

(Continued)

OTHER PUBLICATIONS

DE 198 19 407 A1 Machine Translation.

(Continued)

*Primary Examiner* — Lyle Alexander
(74) *Attorney, Agent, or Firm* — Woodard, Emhardt, Moriarty, McNett & Henry LLP

(57) ABSTRACT

A test strip with a sample chamber is secured to a meter. The sample chamber in the portion of the test strip that extends out of the meter is illuminated by transmitting light from a light source inside the meter internally through the test strip towards the sample chamber. By way of analogy, the test strip acts in a fashion similar to a fiber optic cable or optical wave guide by transmitting the light from the meter to the remotely located sample chamber that extends outside the meter. The user is then able to easily see the sample chamber of the test strip in dark conditions so that the user is able to readily align the sample chamber with the drop of fluid on the skin as well as view the sample chamber in order to ensure proper filling. The light also illuminates a test strip slot into which the test strip is inserted.

19 Claims, 6 Drawing Sheets

U.S. PATENT DOCUMENTS

| | | | |
|---|---|---|---|
| 7,276,027 | B2 | 10/2007 | Haar et al. |
| 7,285,198 | B2 | 10/2007 | Douglas |
| 2003/0207441 | A1 | 11/2003 | Eyster et al. |
| 2005/0009126 | A1 | 1/2005 | Andrews et al. |
| 2005/0023137 | A1 | 2/2005 | Bhullar et al. |
| 2005/0201897 | A1 | 9/2005 | Zimmer et al. |
| 2005/0265094 | A1 | 12/2005 | Harding et al. |
| 2005/0276133 | A1 | 12/2005 | Harding et al. |
| 2006/0099108 | A1 | 5/2006 | List et al. |
| 2006/0100542 | A9 | 5/2006 | Wong et al. |
| 2006/0222567 | A1 | 10/2006 | Kloepfer et al. |
| 2007/0167869 | A1 | 7/2007 | Roe |
| 2007/0255301 | A1 | 11/2007 | Freeman et al. |
| 2010/0021342 | A1 | 1/2010 | Joseph et al. |

FOREIGN PATENT DOCUMENTS

| | | | |
|---|---|---|---|
| EP | 1 918 707 | A2 | 5/2008 |
| EP | 2 377 465 | A1 | 10/2011 |
| WO | WO 01/08551 | A2 | 2/2001 |
| WO | 2005/119234 | A2 | 12/2005 |

OTHER PUBLICATIONS

DE 198 49 539 A1 Machine Translation.

DE 198 57 426 A1 Machine Translation.

International Patent Application No. PCT/EP03/13298 International Search Report mailed Apr. 10, 2004.

Glucometer Elite® Diabetes Care System User Guide, Bayer Corporation, Elkhart, IN, Rev. Jun. 1998.

U.S. Appl. No. 10/008,788, "Fourth Supplemental Information Disclosure Statement", dated Mar. 8, 2007.

International Application No. PCT/EP2009/005233 International Search Report and Written Opinion mailed Oct. 22, 2009.

International Application No. PCT/EP2009/005233 International Preliminary Report on Patentability mailed Oct. 8, 2010.

JP 05-164756 A English Language Abstract.

European Patent Application No. 09 777 286.7 Office Action mailed Jul. 14, 2011.

\* cited by examiner

METHOD AND APPARATUS FOR LIGHTED TEST STRIP

BACKGROUND

The present invention generally relates to systems and methods of testing body fluids.

Home diagnostic testing has been popular with many patients suffering from chronic diseases or disorders, such as high cholesterol or diabetes. However, at times, there are numerous sources that can make testing difficult, thereby reducing testing frequency, which in turn can lead to dangerous or even potentially life-threatening conditions. For diabetics as well as others, their vision may have deteriorated due to age and/or the effects of the disease. This poor vision can make testing difficult. Further, low light conditions, such as occurring in restaurants, outdoors, theatres, doctor's offices, etc., can make testing difficult even for those with normal vision.

For example, the small size of modern test strips can make loading the test strip into the meter in near dark conditions rather difficult. Even in normally well lit rooms, testing can be difficult, especially for those with poor eyesight. For instance, a user might hunch over their finger or other test site during sampling, thereby casting a shadow over the finger. While current test strips are able to accurately analyze smaller fluid samples, positioning the test strip to draw in these smaller samples can be problematic, and seeing if the test strip is properly filled with these small sample volumes can be troublesome as well.

Using external light sources, such as flashlights, to provide light during testing is not a practical option because testing usually requires the use of both hands, and shadowing of the light can still be problematic when trying to view the test strip, the meter, and/or the testing site. Test strip designs have been proposed in which Organic Light Emitting Diodes (OLEDs) are integrated into the test strip so as to light around the sample chamber. However, these designs have several considerable drawbacks, including expense, low/variable light output, testing interference/contamination, and failure to facilitate test strip loading. Thus, there is a need for improvement in this field.

SUMMARY

Typically, the sampling ends of electrochemical test strips stick out from the meter so that they can be easily positioned to collect fluid as well as prevent the meter from being contaminated with blood. However, by sticking out of the meter, illumination of the sample chamber in the sampling end of the test strip can be problematic. The inventors discovered that the sample chamber in the portion of the test strip that extends out of the meter can be illuminated by transmitting light from a light source inside the meter internally through the test strip towards the sample chamber. By way of analogy, the test strip acts in a fashion similar to a fiber optic cable (or optical wave guide) by transmitting the light from the meter to the remotely located sample chamber that extends outside the meter. The user is then able to easily see the sample chamber of the test strip in dark conditions so that the user is able to readily align the sample chamber with the drop of fluid on the skin as well as view the sample chamber in order to ensure proper filling.

By transmitting light through the test strip, the sample chamber of the test strip can be effectively illuminated even when the sample chamber extends well outside of the meter. The shadowing problems created by external light sources are also eliminated because the light emanates from the test strip, rather than being reflected off the test strip. In comparison to the above-mentioned designs in which OLEDs are incorporated into the test strip, this design provides a cost efficient alternative with superior performance. With this design, the test strip does not need to incorporate expensive OLEDs as well as other associated structures, which can also be potential contamination, temperature, and/or electrical interference sources. Having the light source in the meter, rather than in the test strip, facilitates the use of brighter/higher-powered light sources that can enhance visibility in relatively dark ambient or even in normal lighting conditions.

In one aspect, a spacer layer that forms the sides of the sample chamber is made of a light trasmissive material, which is transparent or even semi-transparent, in order to transmit the light from inside the meter to the end of the test strip outside the meter that contains the sample chamber. In other variations, one or more other layers of the test strip can be made from materials that transmit light, inhibit light transmission, or have a combination of light transmission properties.

In a further aspect, the light source is located in the test strip slot or opening where the test strip is connected to the meter. By being located in the test strip slot, the light source is able to not only light the sample chamber in the test strip during sample application, but it is also able to light the test strip slot during loading or unloading so as to assist the user in guiding the test strip into the slot during low ambient light conditions. To put it another way, the same light source used to illuminate the test strip slot during loading also illuminates the test strip during sample application.

In a further aspect, the light source is used to positionally align the test strip in the meter, and in a more specific embodiment, the test strip has an emitter opening into which the light emitter of the meter is received. When the test strip is properly inserted into the meter such that the light emitter is received in the emitter opening of the test strip, the end of the test strip surrounding the sample chamber will brightly illuminate, thereby signalling that the test strip is properly seated. Further, the light emitter acts in a fashion similar to a detent such that the test strip is held properly in place, which in turn prevents the test strip from being accidentally dislodged from the contacts in the meter. For integrated disposables, such as Lancet Integrated Test Strips (LITs), the emitter opening in the test strip provides a fastening point where the test strip can be held while the lancet is actuated to lance the skin. The light emitted from the end of the integrated disposable can also help in aiming the lancet during lancing as well as during fluid collection.

Other aspects concern unique techniques for collecting fluid samples in low ambient light conditions as well as methods of manufacturing test strips and systems for collecting samples in low light conditions.

Other features and benefits will be appreciated from the following detailed description.

DETAILED DESCRIPTION

Figure 1:
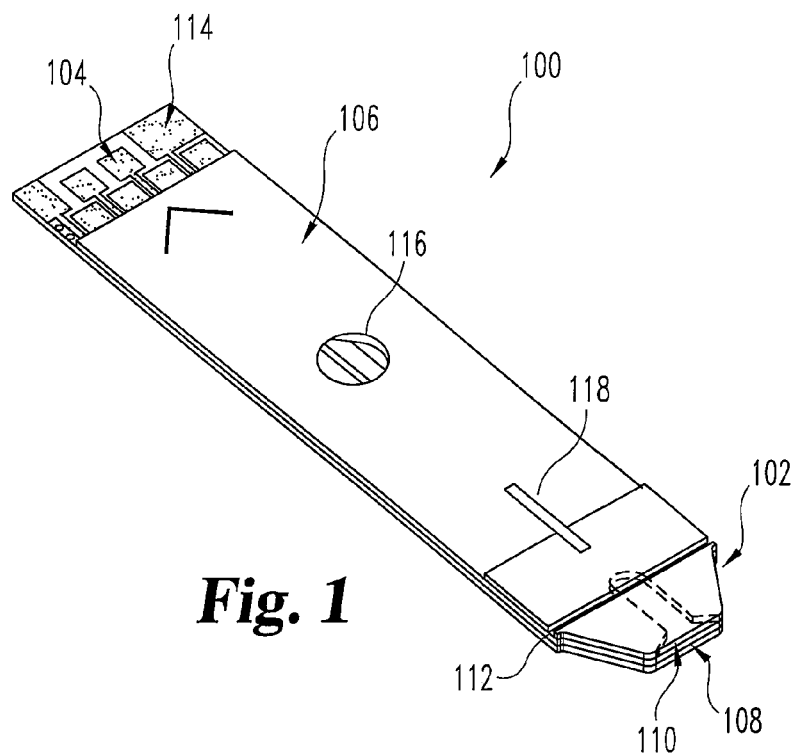
FIG. 1 is a perspective view of a test strip according to one embodiment.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments and any further applications of the principles of the invention as described herein are contemplated as would normally occur to one skilled in the art to which the invention relates.

For the convenience of the reader, it should be initially noted that the drawing in which an element is first introduced is typically indicated by the left-most digit(s) in the corresponding reference number. For example, a component identified with a one-hundred series reference number (e.g., 100, 101, 102, 103, etc.) will usually be first discussed with reference to FIG. 1, and a component with a two-hundred series reference number (e.g., 200, 201, 202, 203, etc.) will usually be first discussed with reference to FIG. 2.

As mentioned above, the system and technique described and illustrated herein addresses the issue of poor visibility during testing, such as in low ambient light conditions, by transmitting light from a light source inside the meter internally through the test strip towards the sampling end of the test strip. The test strip is configured to operate in a fashion somewhat similar to a fiber optic cable such that the light is transmitted longitudinally within the test strip to the sampling end of the test strip that is remotely located outside of the meter. The transported light then irradiates from the test strip such that the various parts of the test strip, like the sample chamber, can be easily viewed. This configuration provides an elegant, inexpensive solution for ensuring that the sampling end is properly lit. This design facilitates the use of brighter/higher powered lights, which in turn increases the brightness of the light emitted from the sampling end of the test strip. The higher powered light sources, which tend to be more expensive, are incorporated into the meter, rather than in the disposable test strip. Thus, the light source can be reused for multiple tests, which in turn reduces the cost of the test strip as well as the overall cost over the life of the system. In one form, the light source is positioned in the test strip slot so that it can also guide the user during test strip insertion. In selected embodiments, the light source can be used to align and/or retain the test strip in the meter. For instance, the test strip in one form has an opening in which the light source is received, and only when the test strip is properly inserted does the test strip become illuminated. For integrated disposables, the light source can be used to hold the test strip in place as the lancet is fired into the skin.

A perspective view of a test strip or biosensor 100 according to one embodiment is illustrated in FIG. 1. As can be seen, the test strip 100 has a sampling end 102 where body fluid is collected, a connection end 104 where the test strip 100 is connected to the meter, and an intermediate or body portion 106 located between the sampling 102 and connection 104 ends. The sampling end 102 has a sample chamber 108 with a fluid collection opening 110 through which the body fluid sample is collected, and the sample is analyzed within the sample chamber 108. At the end generally opposite opening 110, the sampling end 102 has a vent slot 112 from which air is vented from the sample chamber 108. In the illustrated embodiment, the test strip 100 is an end-fill type test strip, but it should be recognized that the test strip 100 can be configured to collect fluid in other manners. The test strip 100 in other forms can be a top-fill and/or a side-fill type test strip, for example. Moreover, the illustrated test strip 100 is an electrochemical type test strip, but it is contemplated that other types of test strips can be used in other embodiments. The connection end 104 includes one or more contacts 114 where the test strip 100 is electrically coupled to the meter. At the intermediate portion 106, the test strip 100 has a light source or emitter opening 116 where the light source member of the meter is received as will be explained in greater detail below. The light source opening 116 in one embodiment has a 1.5 mm diameter, but the light source opening 116 can have a different size in other embodiments. The test strip 100 at the intermediate portion can also include a firing blade relief slot 118 that provides relief for a firing blade when the test strip 100 is incorporated into an integrated disposable. For additional information about the blade relief slot 118, please refer to U.S. Application Publication No. 2007/0167869 A1, which is hereby incorporated by reference in its entirety. In other forms, such as when the test strip 100 is used alone, the relief slot 118 can be omitted from the test strip 100.

Figure 2:
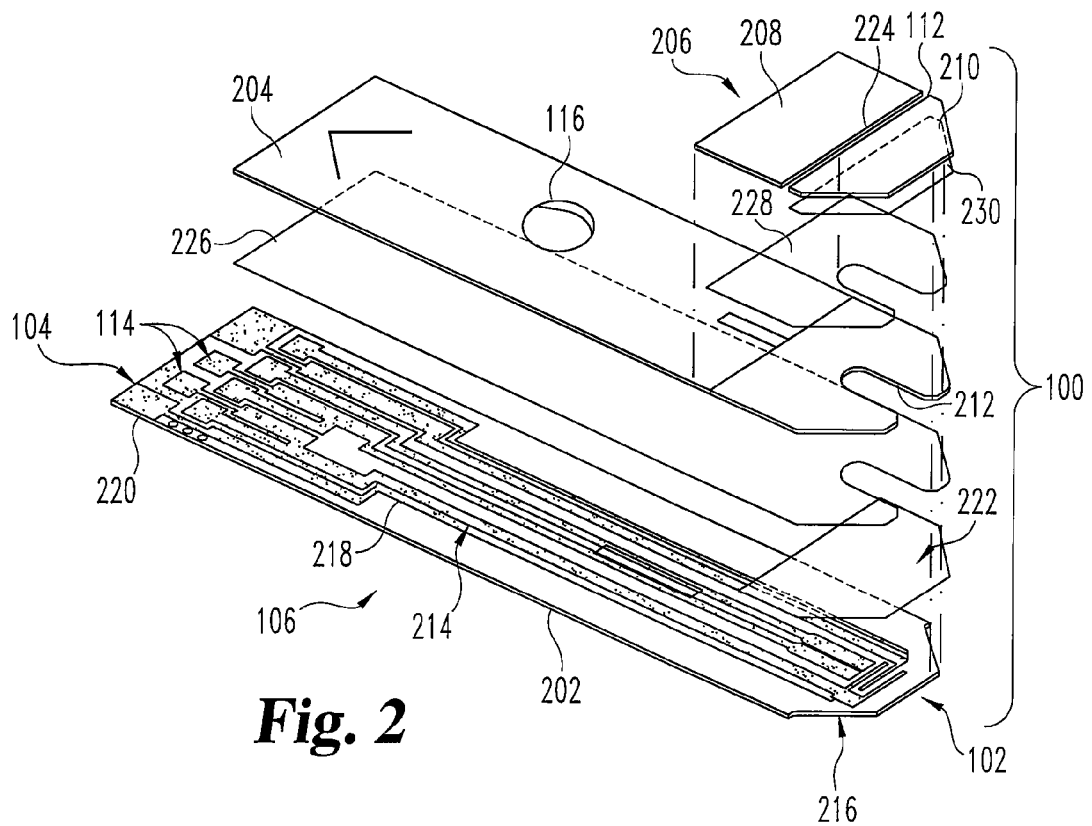
FIG. 2 is an exploded view of the test strip of FIG. 1.

An exploded view of the test strip 100 is depicted in FIG. 2. As shown, the test strip 100 includes a base substrate 202, a spacer layer 204, and a cover layer 206 comprising body cover 208 and chamber cover 210. The spacer layer 204 includes a void portion 212 that forms the sample chamber 108 extending between the base substrate 202 and the cover layer 206. The base substrate 202 carries an electrode system 214 including a plurality of electrodes 216 and electrode traces 218 terminating in contact pads 220. The electrodes 216 are defined as those portions of electrode traces 218 that are positioned within the sample chamber 108. Various configurations of the electrode system 214 may be used. A suitable reagent system 222 overlies at least a portion of the electrodes 216 within the sample chamber 108. The body cover 208 and the chamber cover 210 overlying the spacer layer 204 define a vent slot 224 therebetween. The vent slot 224 communicates with the sample chamber 108 to allow air to escape the chamber 108 as a sample fluid enters the chamber 108 from the edge opening. In one embodiment, adhesive layers 226, 228, 230 are used to join the various layers of the test strip 100 together, but the layers can be joined together in other manners, such as via welding.

To provide contrast when the test strip 100 is lit, the base substrate 202 is generally white, but in other embodiments, the base substrate can have a different color (or even no color). For example, the base substrate 202 can have a gray color in other embodiments. The base substrate 202 includes an insulating material supporting the electrode system 214 and other components. Typically, plastics such as vinyl polymers, polyimides, polyesters, and styrenes provide the electrical and structural properties which are required. Further, because the test strip is preferably mass producible from rolls of material, it is desirable that the material properties be appropriate to have sufficient flexibility for roll processing while also giving a useful stiffness to the finished strip. The base substrate 202 can be selected as a flexible polymeric material such as polyester, especially high temperature polyester materials; polyethylene naphthalate (PEN); and polyimide, or mixtures of two or more of these. Polyimides are available commercially, for example under the trade name Kapton®, from E.I. DuPont de Nemours and Company of Wilmington, Del. (DuPont). In one embodiment, the base substrate material is MELINEX® 329 available from DuPont. The spacer layer 204 is made of a light transmissive material so that the spacer layer 204 is able to transmit light from the light source opening 116 to the sample chamber 108. For instance, the spacer layer 204 can be whole or in part transparent and/or translucent in order to transmit light. Alternatively or additionally, other layers of the test strip 100 can be transparent and/or translucent so as to facilitate the transmission of light to the sample chamber 108. For example, the chamber cover 210 in one embodiment is clear so that the user can readily visualize the blood or other body fluid within the sample chamber 108. In one form, the spacer layer 204 is a clear polyethylene terephthalate (PET), such as sold under the brand names MELINEX® or MYLAR®, that is 4 mils thick. It, however, should be recognized that the spacer layer 204 can be made from other types of materials and can have different dimensions.

Figure 3:
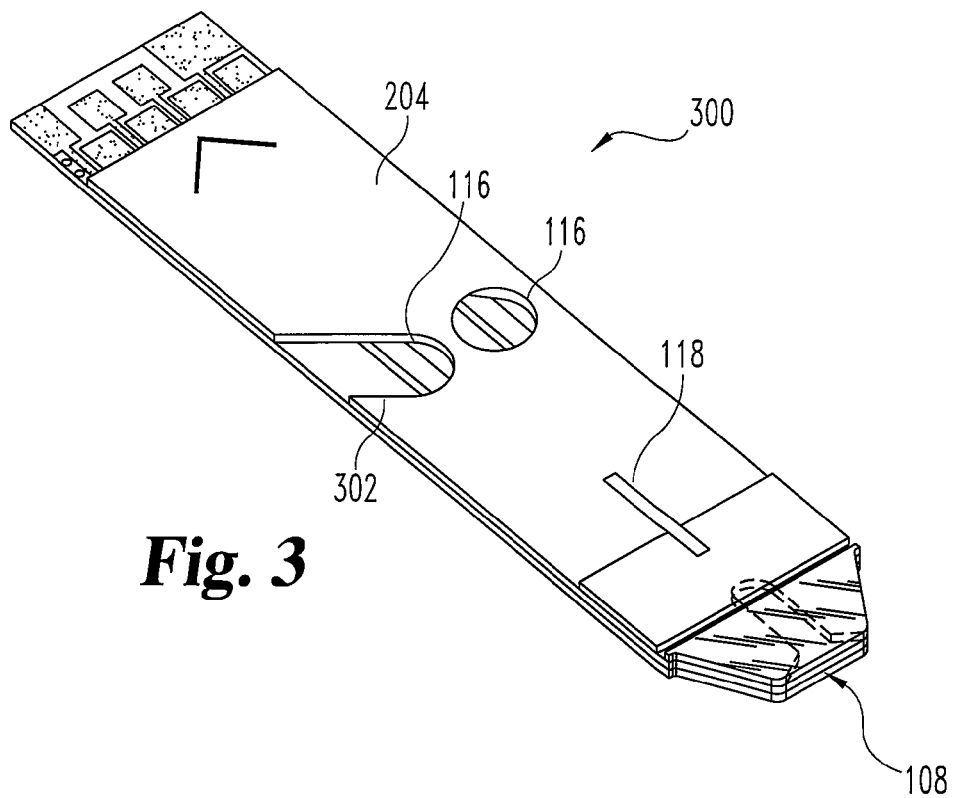
FIG. 3 is a perspective view of a test strip according to a further embodiment.
Figure 4:
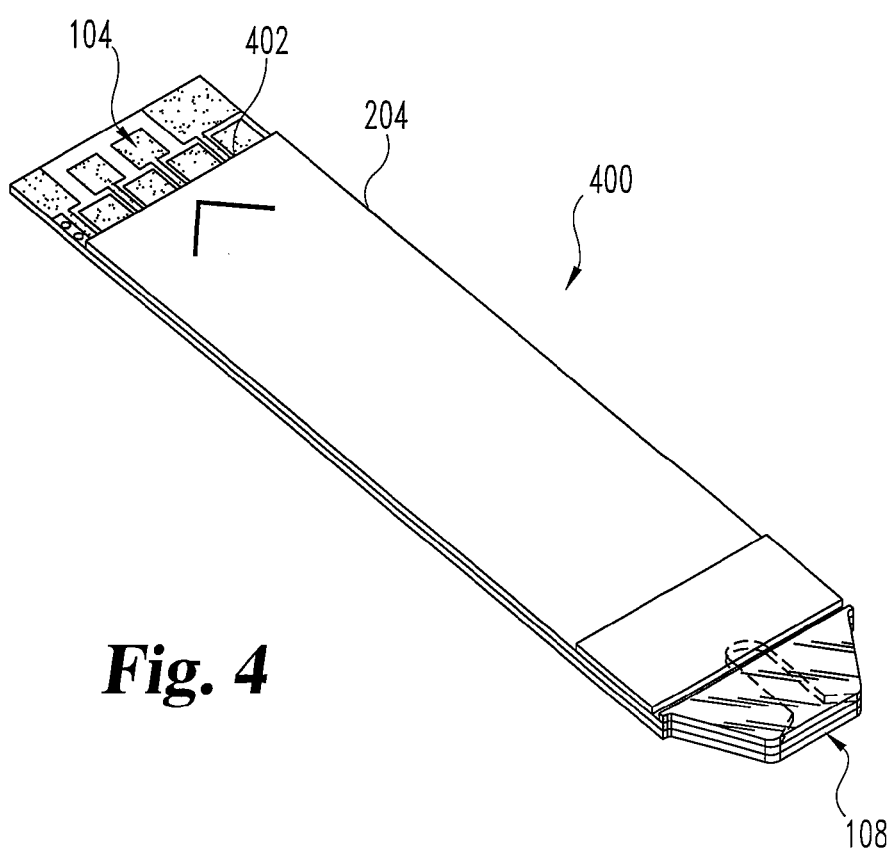
FIG. 4 is a perspective view of a test strip according to still yet another embodiment.

The light source opening 116 in the spacer layer 204 is configured to receive a light source, such as an LED, in the meter. The light source opening 116 can be formed in the spacer layer 204 through any number of manufacturing techniques. For instance, the light source opening 116 can be punched, cut, etched, etc. in the spacer layer 204. In the illustrated embodiment, the spacer layer 204 has a single light source opening 116 with a circular shape. The test strip 100 in other embodiments can include more or less light source openings 116 than shown, and the light source openings can be shaped differently in other embodiments. A perspective view of a test strip 300 with differently configured light source openings 116 according to another embodiment is illustrated in FIG. 3. The test strip 300 in FIG. 3 is very similar in construction with the test strip 100 of FIG. 1, but the test strip 300 in FIG. 3 has two light source openings 116 from which light is transmitted through the spacer layer 204 to the sample chamber 108. With the two light source openings 116, the test strip 300 can be more stably secured in the meter and can increase the brightness of light at the sample chamber 108. In FIG. 3, one of the light source openings 116 is in the form of a notch 302 defined in the spacer layer 204. Again, it should be recognized that the light source openings 116 can be shaped differently in other embodiments. It is even envisioned that the light source openings 116 can be omitted, as is depicted in FIG. 4. A perspective view of a test strip 400 without a light source opening 116 is illustrated in FIG. 4. Instead of using a light source opening 116, the spacer layer 204 of the test strip 400 has a light source edge 402 at the connection end 104. The light source in the meter is placed against (or near) the light source edge 402 so that the light from the light source can be transmitted to the sample chamber 108 via the spacer layer 204. The light source in the illustrated embodiment provides visible light, but other light frequencies can be used so long as visible light is irradiated at the desired location. For example, the sampling end 102 can contain or otherwise be made of a fluorescent material that emits visible light when exposed to ultraviolet light transmitted through the test strip 100 from an ultraviolet light source inside the meter. The added benefit of the ultraviolet light source is that it helps to at least partially sterilize the meter.

Figure 5:
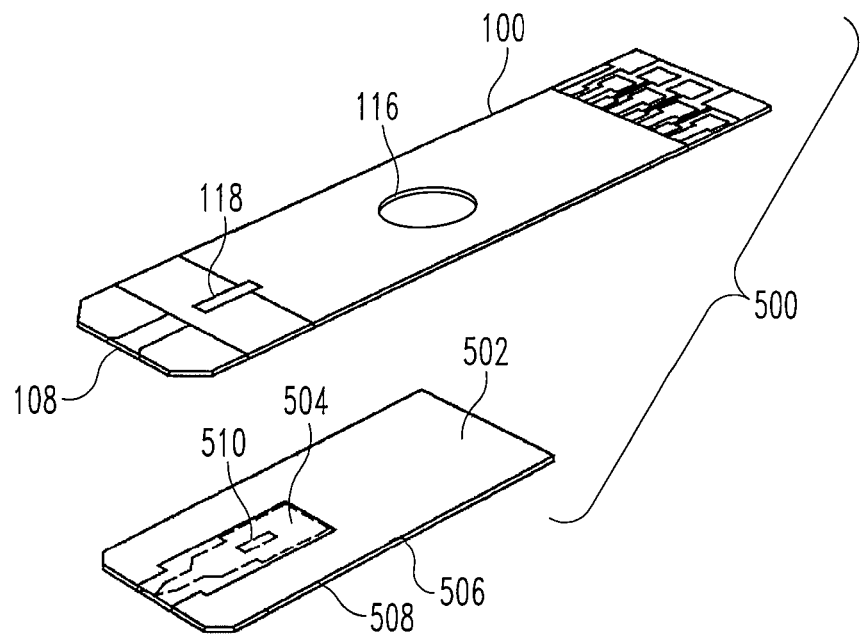
FIG. 5 is an exploded view of an integrated disposable that incorporates the test strip of FIG. 1.
Figure 6:
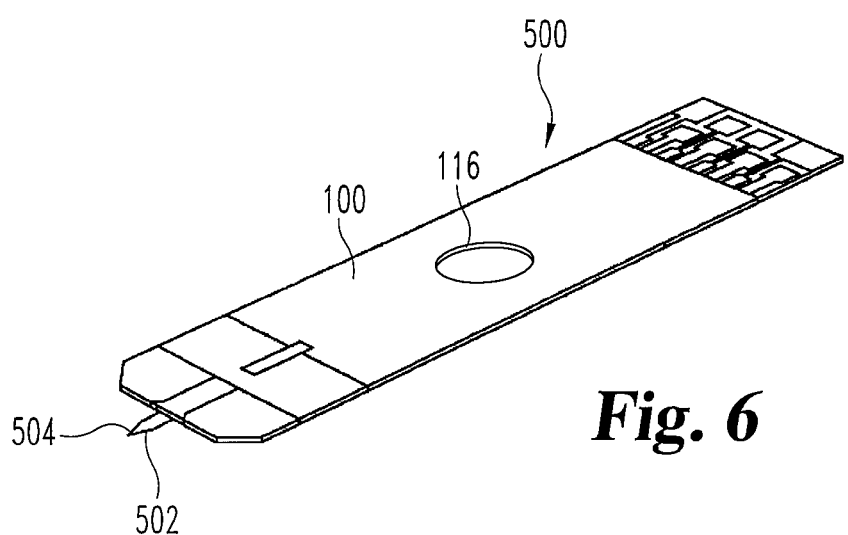
FIG. 6 is a perspective view of the integrated disposable of FIG. 5.

As mentioned before, this ability to remotely illuminate the sample chamber 108 can be incorporated into other types of fluid sampling devices, such as integrated disposables. An example of one such integrated disposable 500 is depicted in FIGS. 5 and 6. The integrated disposable 500 in the illustrated embodiment is an LIT, but other types of integrated devices can incorporate this illumination feature. In the integrated disposable 500, a lancet packet 502 is secured to the test strip 100 of FIG. 1. The lancet packet 502 includes a lancet 504 slidably disposed in a lancet guide 506 and a sterility sheet 508 wrapped around the lancet guide 506 so as to maintain the sterility of the lancet 504. The lancet 504 further includes an engagement opening 510 for coupling the lancet 504 to a firing mechanism in the meter. During lancing, the firing mechanism via the engagement opening 510 extends the lancet 504 from the lancet packet 502. As the lancet 504 extends, the lancet 504 pierces the sterility sheet 508, and after piercing the skin or other tissue, the lancet 504 is retracted back inside the lancet packet 502. For additional information about integrated disposables, please refer to U.S. Application Publication No. 2007/0167869 A1, which is hereby incorporated by reference in its entirety.

Figure 7:
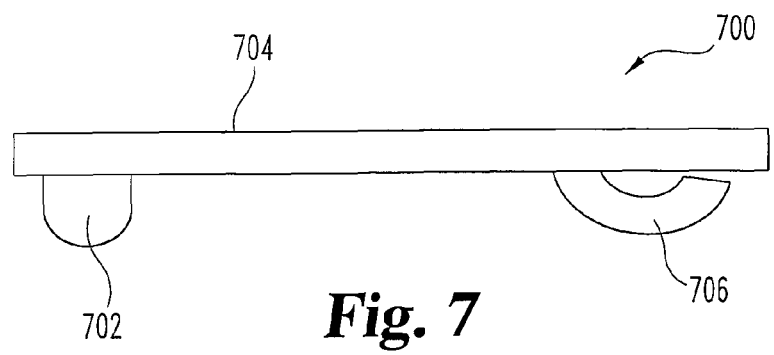
FIG. 7 is a side view of a support subassembly for the light emitter that illuminates the test strip.
Figure 8:
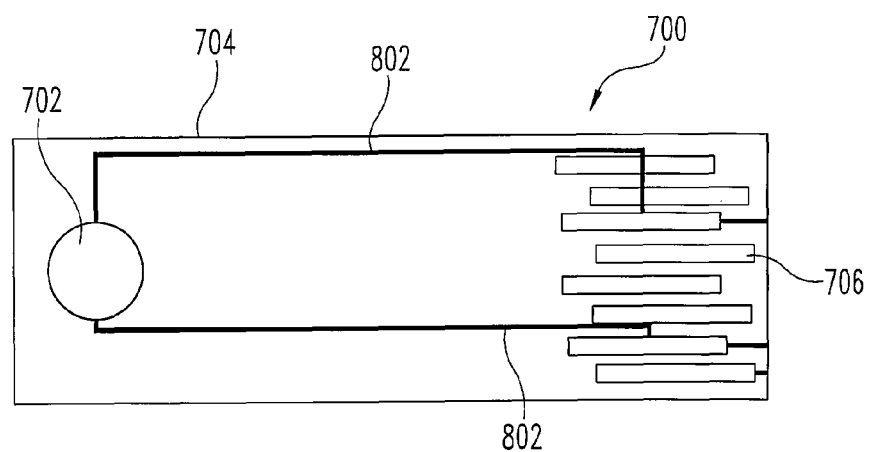
FIG. 8 is a front view of the support subassembly of FIG. 7.
Figure 9:
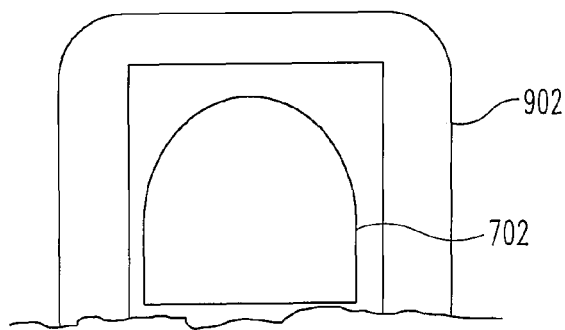
FIG. 9 is an enlarged view of the light emitter on the support subassembly of FIG. 7.

FIGS. 7 and 8 show diagrammatic views of a light source assembly 700 used to illuminate the test strip slot during loading/unloading of the test strip 100, and once the test strip 100 is inserted in the meter, the sample chamber 108. In the illustrated embodiment, the assembly 700 includes a light source 702 mounted on a base 704. Light source 702 can include any type of light source known in the art. By way of nonlimiting examples, the light source 702 can include incandescent lights, fluorescent lights, LEDs, OLEDs, High Intensity Discharge (HID) lamps, etc. The light source 702 can emit a single color or multiple colors. For instance, the light source 702 can emit different colored lights during the various testing phases. As an example, the light source 702 can shine white light during loading/unloading of the test strip 100, red light when the test strip 100 is not properly seated or not completely filled with the fluid sample, and a green light to indicate a successful test. In another example, the light source 702 emits the same white light during every testing phase. The light source 702 can be powered by a wide variety of power sources, like batteries, fuel cells, power grids, generators, etc., and the operation of the light source 702 can be controlled by a microprocessor within the meter, for example. The base 704 in selected embodiments is made of a rigid or flexible circuit board. The base 704 can also be incorporated into the housing or other components of the meter. The assembly 700 further has contacts 706 that are configured to establish electrical connections with the contact pads 220 on the test strip 100. Leads 802 (FIG. 8) on the base 704 are used to power and control the light source 702. As noted before, once the light source 702 is received in the light source opening 116 in the test strip 100, the light source 702 can be used to act like a detent so as to retain the test strip 100 in the meter. To protect the light source 702, an outer covering or shell 902 can cover the light source 702, as is depicted in FIG. 9. In one embodiment, the outer covering 902 is made of molded plastic so as to act like a lens. However, the light source 702 in other embodiments can be uncovered.

Figure 10:
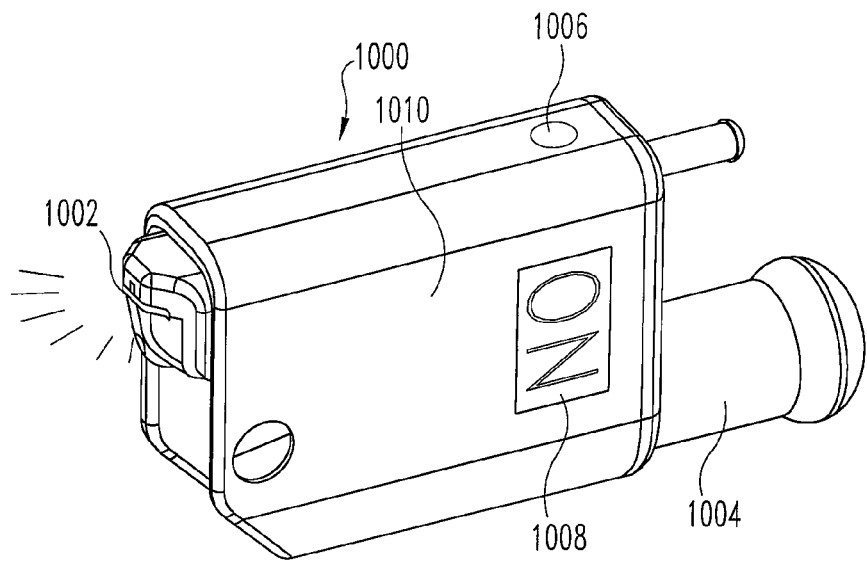
FIG. 10 is a perspective view of a meter according to one embodiment.
Figure 11:
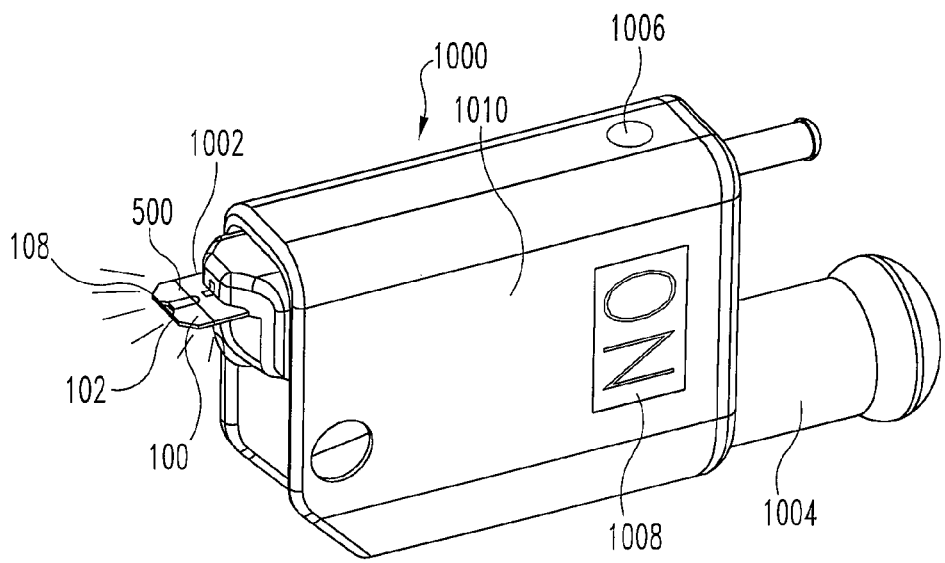
FIG. 11 is a perspective view of the meter of FIG. 10 when the integrated disposable of FIG. 5 is loaded.

A perspective view of a meter 1000 that incorporates the previously-described light source assembly 700 is illustrated in FIG. 10. The meter 1000 is designed to cut the incision and analyze the resulting fluid sample with the integrated disposable 500 of FIG. 5. The meter 1000 includes a test strip slot or opening 1002 where the integrated disposable 500 (or a test strip alone, if so desired) is loaded into the meter 1000. The meter 1000 further incorporates a firing mechanism 1004 for firing the lancet 504 of the integrated disposable 500, a firing button 1006 for firing the firing mechanism 1004, and a display 1008 on a meter housing 1010 that provides the test results along with other information. FIG. 10 shows the state of the meter 1000 before the integrated disposable 500 is loaded. As can be seen, the light source 702 inside the meter 1000 illuminates that test strip slot 1002 before the integrated disposable 500 is loaded. Illuminating the test strip slot 1002 helps the user to locate the slot 1002 during the loading of the integrated disposable 500. Once the integrated disposable 500 is properly loaded, as is shown in FIG. 11, the sample chamber 108 becomes illuminated, thereby indicating that the integrated disposable 500 is ready for testing. Not until the light source 702 is properly seated in the light source opening 116 in the integrated disposable 500 does the sample chamber 108 become brightly illuminated. This helps to promote proper seating of the integrated disposable 500 in the meter 1000. With the test strip 100 in the integrated disposable 500 acting like an optical wave guide, the sampling end 102 of the test strip 100 extending from the meter 1000 is able to be illuminated without the need for an outside light source. In this example, the spacer layer 204 of the test strip 100 has light transmissive properties in order to transmit the light from the light source 702 to the sampling end 102 extending from the meter 1000, but other layers in the test strip 100 can be used to internally transmit the light. This internal illumination avoids the issues of poor illumination due to shadowing and/or distant lighting. With this illumination configuration, the user is able to readily position the sample chamber 108 to collect fluid, and the user is able to easily see if the sample chamber 108 is properly filled. Moreover, this configuration allows more powerful and/or sophisticated light sources to be used in an inexpensive manner because the light source 702 can be reused to conduct multiple tests.

Figure 12:
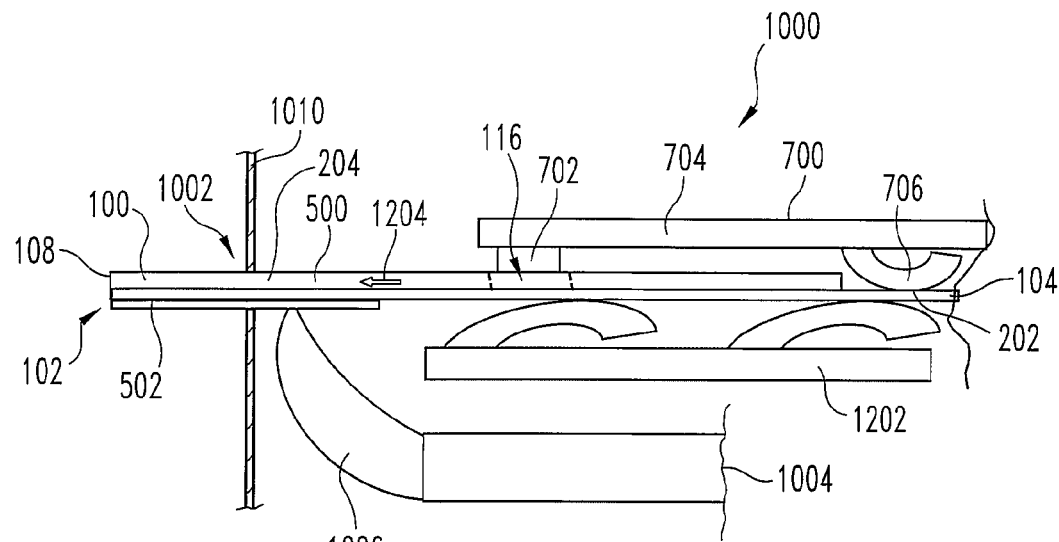
FIG. 12 is a side enlarged view of the integrated disposable of FIG. 5 connected to a connection assembly according to another embodiment.

FIG. 12 illustrates the interface when the integrated disposable 500 is inserted into the meter 1000. As illustrated, the integrated disposable 500 is slid between the light source assembly 700 and a spring-biased support 1202 until the light source 702 engages the light source opening 116. At that point, the light source 702 is then able to transmit light in the spacer layer 204 in direction 1204 to the sample chamber 108 of the test strip 100. It is contemplated that in other embodiments the light source 702 does not need to be seated in the light source opening 116 before illumination of the sample chamber 108 takes place. While the integrated disposable 500 is loaded, an actuation blade 1206 of the firing mechanism 1004 punctures the lancet packet 502 so as to engage the engagement opening 510 in the lancet 504 (FIG. 5). The contacts 706 in the meter establish electrical connections with the contact pads 220 on the test strip 100. Once seated in the light source opening 116, the light source 702 is able to hold the test strip 100 in place as the actuation blade 1206 actuates the lancet 504. The light shining from the now illuminated integrated disposable 500 can be used to aim or position the integrated disposable 500 at the proper site. With the internally illuminated sample chamber 108 extending from the meter 1000, the user is able to easily visualize the fluid collection site and ensure that the fluid properly fills the sample chamber 108, even in low light conditions. Once the test is complete, the user removes the integrated disposable 500 from the meter 1000 such that the light source 702 in the meter 1000 is able to re-illuminate the test strip slot 1002. During removal, the user pulls on the integrated disposable 500 so that the light source 702 disengages from the light source opening 116 in a fashion similar to a detent mechanism. Once the integrated disposable 500 is disengaged from the light source 702, the user is then able to pull the integrated disposable 500 completely from the meter 1000. With the integrated disposable 500 removed, the light source 702 is then able to illuminate the test strip slot 1002.

Figure 13:
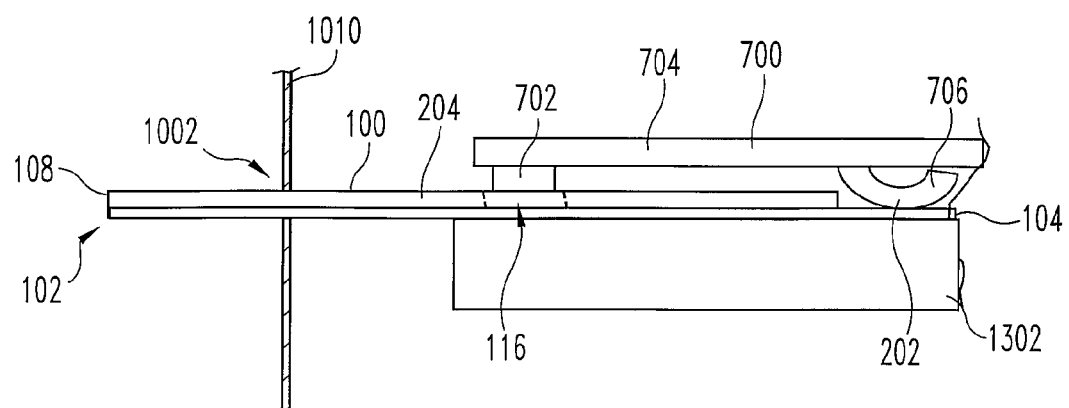
FIG. 13 is a side enlarged view of the test strip of FIG. 1 connected to a connection assembly according to one embodiment.

FIG. 13 shows a similar arrangement when the test strip 100 is loaded into a meter. Before the test strip 100 is loaded, the light source 702 illuminates the test strip slot 1002. During insertion of the test strip 100, the base 704 of the light source assembly slightly bends or deflects as the test strip 100 is slid between a support 1302 and the light source assembly 700. Eventually, the light source opening 116 in the test strip 100 reaches the light source 702 such that the light source 702 snaps into the light source opening 116, thereby holding the test strip 100 in place. At the same time, the contacts 706 of the light source assembly 700 establish electrical connections with the contact pads 220 on the test strip 100. Via the transparent or translucent spacer layer 204, light from the light source 702 is transmitted to the sampling end 102 that extends from the test strip slot 1002. The user is then able to easily visualize the body fluid as it fills the sample chamber 108. Once the test is complete, the user can remove and discard the test strip 100. With the test strip 100 removed, the light source 702 once again illuminates the test strip slot 1002. To remove the test strip 100, the user pulls on the test strip 100 such that the light source 702 releases from the light source opening 116 in a fashion similar to a detent type mechanism. Once the test strip 100 is released from the light source 702, the test strip 100 is pulled out of the test strip slot 1002, and the light source 702 is then able to illuminate the test strip slot 1002.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected.

What is claimed is:

1. An apparatus, comprising:
   a meter including a light source; and
   a test strip coupled to the meter, the test strip having a sampling end with a sample chamber extending outside the meter, at least a portion of the test strip being made of a light transmissive material to transmit light from the light source to the sampling end, the test strip having an intermediate portion adjacent the sampling end, the intermediate portion including a light source opening in which the light source is received.

2. The apparatus of claim 1, further comprising:
   the meter including a test strip opening in which the test strip is received; and
   the light source being positioned in the meter to illuminate the test strip opening.

3. The apparatus of claim 1, further comprising:
   an integrated disposable that includes the test strip and a lancet connected to the test strip;
   the meter including a firing mechanism for firing the lancet into tissue; and
   the light source being received in the light source opening to hold the test strip in place as the lancet is fired.

4. The apparatus of claim 1, further comprising:
   the test strip including a spacer layer that at least in part defines a sample chamber; and the spacer layer being made of the light transmissive material to transmit light from the light source to illuminate the sample chamber.

5. The apparatus of claim 4, further comprising:
the test strip including a cover layer covering the sample chamber, the cover layer being clear for visualization of the sample chamber.

6. The apparatus of claim 1, further comprising:
the sampling end of the test strip including a fluorescent material that fluoresces in presence of the light from the light source.

7. The apparatus of claim 1, further comprising:
a light source shell covering the light source.

8. The apparatus of claim 1, further comprising:
the test strip including a light source edge through which the light from the light source is transmitted to the sampling end.

9. The apparatus of claim 1, further comprising:
the light source being configured to emit different colors depending on stage of testing.

10. The apparatus of claim 1, further comprising:
wherein the light source received in the light source opening demountably retains the test strip in the meter.

11. An apparatus, comprising:
an integrated disposable including a lancet and a test strip coupled to the lancet, the test strip having a sampling end and an intermediate section adjacent the sampling end, the intermediate section including a light source opening, the test strip including a spacer layer made of light transmitting material that defines a sample chamber in the sampling end; and
a meter having a light source inserted in the light source opening of the test strip to retain the test strip during lancing, the light source being configured to illuminate the spacer layer for allowing a user to visually detect fill sufficiency of the sample chamber.

12. The apparatus of claim 11, further comprising:
the meter including a slot in which the integrated disposable is received; and
the light source being positioned to illuminate the slot.

13. A method, comprising:
loading a test strip in a meter with a sampling end of the test strip extending outside the meter, the sampling end having a sample chamber;
shining light from a light source inside the meter into a light source opening located in an intermediate section of the test strip;
illuminating the sampling end and the sample chamber of the test strip that extend outside the meter by transmitting light from the light source internally through the test strip to the sampling end of the test strip; and
retaining the test strip in the meter by inserting the light source into the light source opening in the test strip.

14. The method of claim 13, further comprising:
lighting a test strip slot in the meter with the light source; and
said loading the test strip including inserting the test strip in the test strip slot.

15. The method claim 14, further comprising:
emitting a first color from the light source during said lighting the test strip slot; and
emitting a second color that is different from the first color during said illuminating the sampling end of the test strip.

16. The method of claim 13, further comprising:
wherein the test strip includes a lancet to form an integrated disposable;
aiming the lancet by shining the light from the sampling end of the test strip onto an incision site; and
cutting an incision at the incision site by firing the lancet while the light source holds the test strip in place.

17. The method of claim 13, further comprising:
wherein the test strip has a spacer layer made of light transmissive material that at least in part defines a sample chamber at the sampling end of the test strip; and
said illuminating the sampling end of the test strip including shining the light through the spacer layer to light the sample chamber.

18. The method of claim 13, further comprising:
wherein the sampling end of the test strip includes a sample chamber;
drawing body fluid into the sample chamber; and
detecting fill sufficiency of the body fluid in the sample chamber by looking at the sample chamber illuminated by the light source.

19. The method of claim 13, further comprising:
wherein the sampling end includes fluorescent material; and
said illuminating the sampling end of the test strip including fluorescing the fluorescent material with the light from the light source.

* * * * *